United States Patent [19]

Jung et al.

[11] Patent Number: 5,527,934

[45] Date of Patent: Jun. 18, 1996

[54] BIS(DICHLOROORGANOSILYL)ALKANES AND THEIR PREPARATION METHODS

[75] Inventors: Il N. Jung; Bong W. Lee; Mi-Yeon Suk, all of Seoul, Rep. of Korea

[73] Assignee: Korea Institute of Science and Technology, Seoul, Rep. of Korea

[21] Appl. No.: 493,453

[22] Filed: Jun. 23, 1995

[30] Foreign Application Priority Data

Jun. 24, 1994 [KR] Rep. of Korea .................. 14634/1994

[51] Int. Cl.$^6$ ........................................................ C07F 7/08
[52] U.S. Cl. ........................... 556/431; 556/435; 556/415
[58] Field of Search ...................................... 556/431, 435, 556/415

[56] References Cited

U.S. PATENT DOCUMENTS

| | | | |
|---|---|---|---|
| 3,296,296 | 1/1967 | Webster | 556/435 |
| 3,304,320 | 2/1967 | Spencer | 556/431 |
| 4,647,682 | 3/1987 | Panster et al. | 556/431 |
| 4,861,901 | 8/1989 | Lau et al. | 556/435 X |
| 4,902,368 | 2/1990 | Oldham | 556/431 X |
| 5,206,402 | 4/1993 | McVannel et al. | |
| 5,233,069 | 8/1993 | Jung et al. | 556/435 |
| 5,235,083 | 8/1993 | Jung et al. | |
| 5,338,876 | 8/1994 | Jung et al. | |

OTHER PUBLICATIONS

M. Kumada, K. Naka, and Y. Yamamoto, "Preparation of some bis(fluorodimethylsilyl)alkanes", 1964, pp. 871–874.

K. B. Adrianov, A. A. Zhdanov, and V. A. Odinets, "Addition of Aromatic Derivatives to Vinylmethyldichlorosilane", 1961.

K. A. Andrianov, L. M. Volkaova, and N. V. Delazari, "Synthesis and Conversions of 2,2, 6-trimethyl-6-chloro-and 2,6-dimethyl-2, 6-dichloro-1-oxa-2,6-disilacyclohexanes", 1968.

Bong Woo Lee, Bok Ryul Yoo, Sun–Il Kim, and Il Nam Jung, "Friedel–Crafts Alkylation of Substituted Benzenes of Allydichlorosilane", 1994, pp. 1312–1316.

E. Y. Lukevits and M. G. Voronkov. "Organic Insertion Reactions of Group IV Elements", 1966.

*Primary Examiner*—Paul F. Shaver
*Attorney, Agent, or Firm*—Oblon, Spivak, McClelland, Maier & Neustadt

[57] ABSTRACT

This invention relates to bis(dichloroorganosilyl)alkenes represented by the formula III and a process for the preparation of the compounds of formula III which comprises hydrosilylating bis(dichlorosilyl)methanes of formula I with organoolefins or organosilylolefins of formula II in the presence of chloroplatinic acid catalyst;

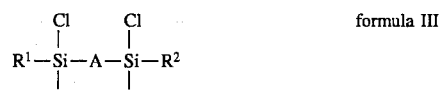

formula III

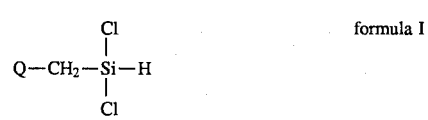
formula I

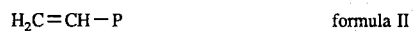
formula II wherein $R^1$ and $R^2$ are same or different and can be —$(CH_2)_2R^3$ (wherein $R^3$ represents Ph, —$CH_2Cl$, —$(CH_2)_yCH_3$ (y=0–15), —$CF_3$, —$CH_2CF_3$, —$SiMe_mCl_{3-m}$ (m=0–3), —CN, —$CH_2CN$, —(p-Ph)$CH_2Cl$ or 3-cyclohexenyl group) or (X—Ph)CH(CH$_3$)CH$_2$— (wherein X represents hydrogen, $C_1$-$C_4$ alkyl, phenyl, fluoro, chloro or bromo group); or $R^1$ is —$CH_3$ or —$(CH_2)_2R^3$ (wherein $R^3$ is same as defined above) and $R^2$ is (X—Ph)CH(CH$_3$)CH$_2$— (wherein X is same as defined above); A is —$(CH_2)_n$— (n=1, 2, 3, 6, 8), or —$(CH_2)_2Ph(CH_2)_2$—; Q represents —$SiHCl_2$ or

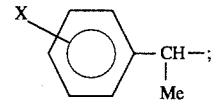

X represents hydrogen, $C_1$-$C_4$ alkyl, phenyl, fluoro, chloro or bromo group; P can be $R^3$, —$CH_2$— $SiCl_2$—$(CH_2)_2$—$R^3$, —B—$SiCl_2CH_3$, or D—CH=CH$_2$, wherein $R^3$ is Ph, —CH$_2$Cl, —$(CH_2)_yCH_3$ (y=0–15), —$CF_3$, —$CH_2CF_3$, —SiMe$_mCl_{3-m}$ (m=0–3), —CN, —$CH_2CN$, —(p-Ph)—$CH_2Cl$ or 3-cyclohexenyl group (B can be —$(CH_2)_n$—(wherin n=4 or 6) or —Ph(CH$_2$)$_2$— and D can be —$(CH_2)_2$— or —Ph—).

12 Claims, No Drawings

BIS(DICHLOROORGANOSILYL)ALKANES AND THEIR PREPARATION METHODS

FIELD OF THE INVENTION

The present invention relates to bis(dichloroorganosilyl)alkanes represented by formula III;

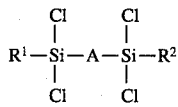
formula III wherein $R^1$ and $R^2$ are same or different and can be —$(CH_2)_2R^3$ (wherein $R^3$ represents Ph, —$CH_2Cl$, —$(CH_2)_yCH_3$(y=0–15), —$CF_3$, —$CH_2CF_3$, —$SiMe_mCl_{3-m}$(m=0–3), —CN, —$CH_2CN$, —(p-Ph)$CH_2Cl$ or 3-cyclohexenyl group) or (X—Ph)CH($CH_3$)$CH_2$— (wherein X represents hydrogen, $C_1$-$C_4$ alkyl, phenyl, fluoro, chloro or bromo group); or $R^1$ is —$CH_3$ or —$(CH_2)_2R_3$ (wherein $R^3$ is same as defined above) and $R^2$ is (X—Ph)CH($CH_3$)$CH_2$— (wherein X is same as defined above); and A can be —$(CH_2)_n$— (n=1, 2, 3, 6 or 8) or —$(CH_2)_2Ph(CH_2)_2$—.

The present invention also relates to a process for the preparation of bis(dichloroorganosilyl)alkanes of formula III which comprises hydrosilylating bis(dichlorosilyl)methanes of formula I with organoolefins or organosilylolefins of formula II in the presence of chloroplatinic acid catalyst;

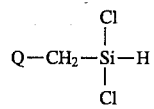
formula I

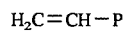
formula II wherein Q represents —$SiHCl_2$ or

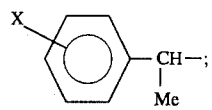

X represents hydrogen $C_1$-$C_4$ alkyl, phenyl, fluoro, chloro or bromo group; and P can be $R^3$, —$CH_2SiCl_2(CH_2)_2R^3$, —B—$SiMeCl_2$, or D—CH=$CH_2$, wherein $R^3$ represents Ph, —$CH_2Cl$, —$(CH_2)_yCH_3$(y=0–15), —$CF_3$, —$CH_2CF_3$, —$SiMe_mCl_{3-m}$(m=0–3), —CN, —$CH_2CN$, —(p-Ph)$CH_2Cl$ or 3-cyclohexenyl group (B can be —$(CH_2)_n$— (n=4 or 6) or —Ph$(CH_2)_2$—; and D can be —$(CH_2)_2$— or —Ph—). The bis(chloroorganosilyl)alkanes according to the present invention are important starting materials for various silicones.

DESCRIPTION OF THE CONVENTIONAL ART

Mcvannel and his co-workers reported the preparation method of 1-alkenylmethyldichlorosilanes in good yield by hydrosilylating α,ω-alkadienes with methyldichlorosilane in the presence of chloroplatinic acid catalyst.(Mcvannel, D. E.; Wall, K. J. U.S. Pat. No. 5,206,402);

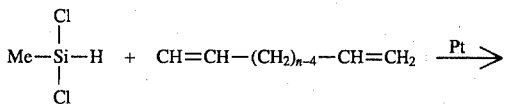

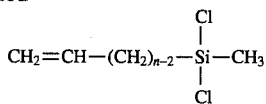

wherein n=6 or 8.

Yamamodo and his co-workers reported the preparation method of bis(dichloromethylsilyl)hexane in good yield by hydrosilylating 1, 5-hexadiene with methyldichlorosilane in the presence of chloroplatinic acid catalyst. The by-product was 5-hexenylmethyldichlorosilane. (Kumada, Y.; Naka, K.; Yamamodo, Y. Bull. Chem. Soc. Jpn. 1964.37.871)

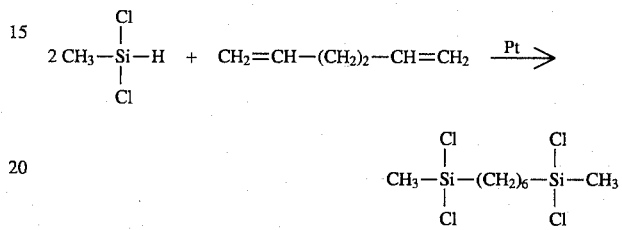

Odinets and his co-workers reported the preparation method of bis(dichloromethylsilyl)diethylbenzenes comprising alkylating α-phenyl-ω-(dichloromethylsilyl)ethane with vinyldichloromethylsilane in the presence of aluminum chloride catalyst. (Odinets, V. A.; Zhdanov, A. A.; Andrianov, K. B. Zh. Obshch. Khim. 1961.31.4033)

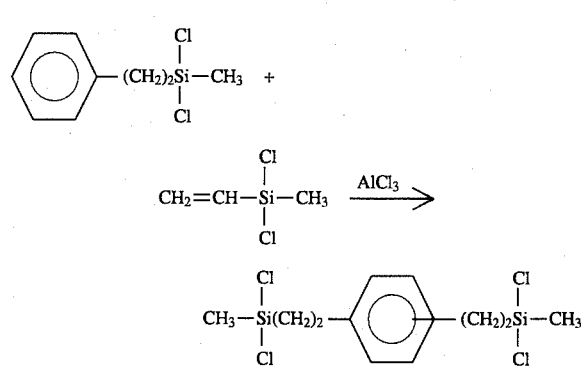

Andrianov and his co-workers reported the preparation method of 1,3-bis(dichloromethylsilyl)propanes in good yield by hydrosilylating allyldichloromethylsilane with methyldichlorosilane in the presence of chloroplatinic acid catalyst. (Andrianov, K. A.; Vokova, L. M.; Delazari N. V. Khim. Geterotsikl. Soedin. 1968.2.222)

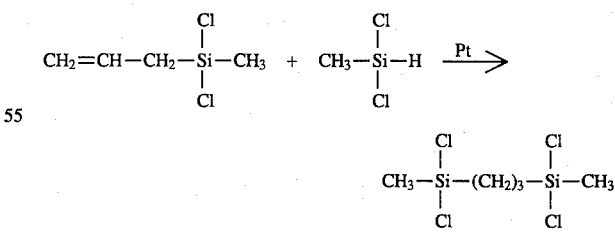

The present applicant reported a process for preparing bis(silyl)alkanes, a starting material of the present invention, having two dichorosilyl groups at the both ends by directly reacting a mixture of organic dichlorides having a chloro at each ends of its molecule and hydrogen chloride or alkyl chloride being capable of generating the hydrogen chloride during its reaction with metallic silicon in the presence of copper catalyst at a temperature from 250° C. to 350° C. (U.S. Pat. No. 5,235,083 (Aug. 10. 1993))

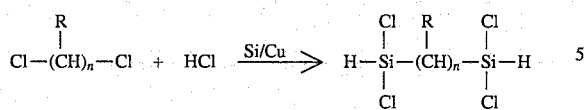

The present applicant also reported a preparation method of allylchlorosilanes, a starting material of the present invention, by directly reacting silicon metal simultaneously with allyl chloride and hydrogen chloride in the presence of copper catalyst at a temperature from 220° C. to 350° C. Allyldichlorosilane was obtained as the major product when 0.5% of cadmium respective to the total contact mass was used. When sufficient hydrogen chloride was added, diallyldichlorosilane was not formed. This eliminated the polymerization problem of diallyldichlorosilane involved in the direct synthesis. (U.S. Pat. No. 5,338,876 (Aug. 16, 1994))

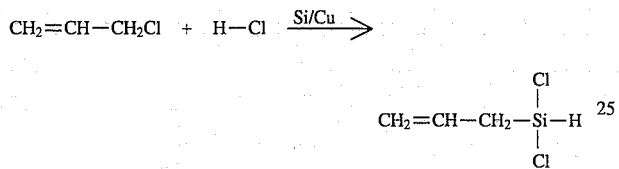

The present inventors reported the preparation method of allylalkylsilanes by hydrosilylating allyldichlorosilane with olefins or cyclohexene in the presence of chloroplatinic acid or active nickel metal catalyst. (Korean Patent Application number 93-26069 (Dec. 17, 1993));

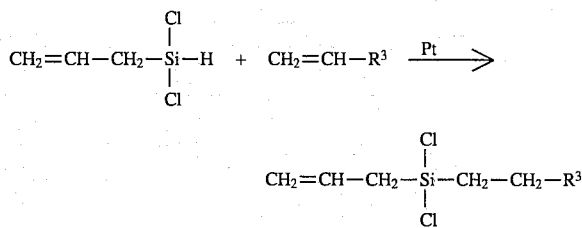

wherein $R^3$ can be Ph, —$CH_2Cl$, —$(CH_2)_yCH_3$ (y=0–15), —$SiMe_mCl_{3-m}$ (m=0–3), —$CF_3$, —$CH_2CF_3$, —CN, —$CH_2CN$, —(p-Ph)$CH_2Cl$ or 3-cyclohexenyl group.

The present inventors also reported the preparation method of (2-arylpropyl)-dichlorosilane, a starting material of the present invention, by the Friedel-Crafts alkylation of various substituted aromatic compounds with allyldichlorosilane in the presence of Lewis acid catalysts. (Lee, B. W.; Yoo, B. R.; Kim, S. I.;Jung, I. N. *Organometallics*. 1994, 13, 1312) The electron donating substituents facilitated the alkylation, while the electron withdrawing substituents retarded.

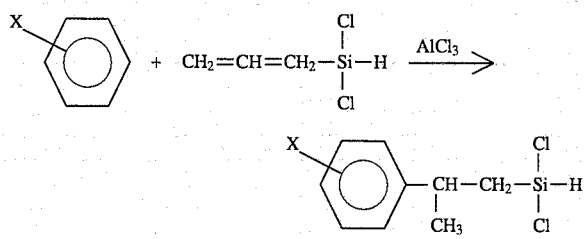

SUMMARY OF THE INVENTION

The present invention relates to bis(dichloroorganosilyl)alkanes represented by formula III;

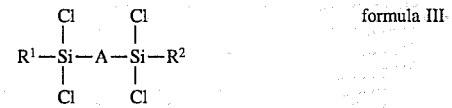

formula III wherein $R^1$ and $R^2$ are same or different and can be —$(CH_2)_2R^3$ (wherein $R^3$ represents Ph, —$CH_2Cl$, —$(CH_2)_yCH_3$(y=0–15), —$CF_3$, —$CH_2CF_3$, —$SiMe_mCl_{3-m}$(m=0–3), —CN, —$CH_2CN$, —(p-Ph)$CH_2Cl$ or 3-cyclohexenyl group) or (X—Ph)CH($CH_3$)$CH_2$— (wherein X represents hydrogen, $C_1$-$C_4$ alkyl, phenyl, fluoro, chloro or bromo group); or $R^1$ is —$CH_3$ or —$(CH_2)_2R_3$ (wherein $R^3$ is same as defined above) and $R^2$ is (X—Ph)CH($CH_3$)$CH_2$— (wherein X is same as defined above); and A can be —$(CH_2)_n$— (n=1, 2, 3, 6 or 8) or —$(CH_2)_2Ph(CH_2)_2$—.

The present invention also relates to a process for the preparation of bis(dichloroorganosilyl)alkenes of formula III which comprises hydrosilylating bis(dichlorosilyl)methanes of formula I with organoolefins or organosilylolefins of formula II in the presence of chloroplatinic acid catalyst;

formula I

formula II wherein Q represents —$SiHCl_2$ or

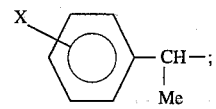

X represents hydrogen, $C_1$-$C_4$ alkyl, phenyl, fluoro, chloro or bromo group; and P can be $R^3$, —$CH_2SiCl_2(CH_2)_2R^3$, —B—$SiMeCl_2$, or D—CH=$CH_2$, wherein $R^3$ represents Ph, —$CH_2Cl$, —$(CH_2)_yCH_3$ (y=0–15), —$CF_3$, —$CH_2CF_3$, —$SiMe_mCl_{3-m}$(m=0–3), —CN, —$CH_2CN$, —(p-Ph)$CH_2Cl$ or 3-cyclohexenyl group (B can be —$(CH_2)_n$—(n=4 or 6) or —Ph($CH_2$)$_2$—; and D can be —$(CH_2)_2$— or —Ph—). The bis(chloroorganosilyl)alkanes according to the present invention are important starting materials for various silicones.

DETAILED DESCRIPTION OF THE INVENTION

The hydrosilylation reactions can be carried out in most of organic solvent, but it also proceeds in neat condition. The hydrosilylation can occur, but proceeds better in the presence of noble metal catalysts such as platinum and chloroplatinic acid. The most common catalyst is chloroplatinic acid and used as a solution in iso-propanol. Besides platinum and its inorganic complexes, inorganic compounds of palladium, nickel, rhodium, ruthenium, copper, and tin were used in the hydrosilylation, depending upon the nature of the olefins. The organic catalysts other than metallic or inorganic compounds such as triethylamine, triphenylphosphine, or dimethylformamide may also be used. (Lukevites, E. Y.; Voronkov, M. G. "*Organic Insertion Reaction of Group IV Elements*" Consultants Bureau, New York, 1966)

All the hydrosilylation reaction was carried out under inert atmosphere. To complete the reaction, heating may be carried out for certain period of time and then the products may be fractionally distilled at atmosphere or under vacuum. The products were identified by ¹H-NMR(300 MHz).

In the present invention, hydrosilylation reactions can be run in standard laboratory glasswares or commercial equipments, under inert atmosphere, with external heating and cooling, stirring, and incremental addition of the starting silanes or olefins.

In a typical preparation, 2-(X-phenyl)propyl}dichlorosilanes and chloroplatinic acid catalyst are placed in the reactor under inert atmosphere. The allylalkylsilanes is the slowly added to the solution with stirring. Although the reaction is exothermic, it may be necessary to maintain to reflux with continuously carrying out external heating.

The hydrosilylation gave better yields when organodienes were added slowly to a mixture of 2-(X-phenyl)propyl}dichlorosilane and chloroplatinic acid solution in isopropanol to keep excess silanes with respect to dienes.

As an embodiment of the present invention, bis(dichloroorganosilyl)methanes of formula III can be prepared by hydrosilylating bis(dichlorosilyl)methane of formula I-1 with organoolefin of formula II-1 in the presence of hydrosilylation catalyst such as chloroplatinic acid or metallic nickel. The products are bis(dichloroorganosilyl)methanes of formula III, wherein A is —CH$_2$—, and R$^1$ and R$^2$ are same or different and can be —(CH$_2$)$_2$R$^3$ (wherein R$^3$ represents Ph, —CH2Cl, —(CH$_2$)$_y$CH$_3$(y=0–15), —CF$_3$, —CH$_2$CF$_3$, —SiMe$_m$Cl$_{m-m}$(m=0–3), —CN, —CH$_2$CN, —(p-Ph)CH$_2$Cl or 3-cyclohexenyl group).

$$\underset{\text{formula I-1}}{\text{H}-\underset{\underset{\text{Cl}}{|}}{\overset{\overset{\text{Cl}}{|}}{\text{Si}}}-\text{CH}_2-\underset{\underset{\text{Cl}}{|}}{\overset{\overset{\text{Cl}}{|}}{\text{Si}}}-\text{H}} + \underset{\text{formula II-1}}{\text{CH}_2=\text{CH}-\text{R}^3} \xrightarrow{\text{Pt}}$$

$$\text{R}^3\text{CH}_2\text{CH}_2-\underset{\underset{\text{Cl}}{|}}{\overset{\overset{\text{Cl}}{|}}{\text{Si}}}-\text{CH}_2-\underset{\underset{\text{Cl}}{|}}{\overset{\overset{\text{Cl}}{|}}{\text{Si}}}-\text{CH}_2\text{CH}_2-\text{R}^3$$

As an another embodiment of the present invention, α-[{2-(X-phenyl)propyl} dichlorosilyl]-ω-(dichloromethylsilyl)ethanes can be prepared by hydrosilylating {2-(X-phenyl)propyl}dichlorosilanes of formula I-2 (wherein X is H, C$_1$-C$_4$ alkyl, phenyl, fluoro, chloro or bromo group) with vinyldichlorosilane of formula II-2 in the presence of chloroplatinic acid catalyst. The products are the compounds of formula III, wherein A is —(CH$_2$)$_2$—, R$^1$ is —CH$_3$, and R$^2$ is (X—Ph)CH(CH$_3$)CH$_2$— (X is same as defined above.}

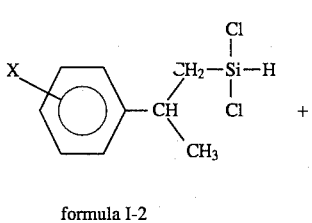

formula I-2

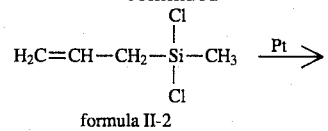

formula II-2

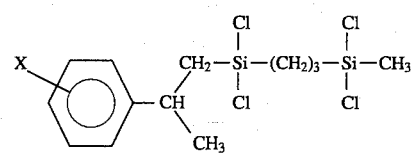

As an another embodiment of the present invention, α-[{2-(X—phenyl)propyl}dichlorosilyl]-ω-{(alkyl)dichlorosilyl}propanes can be prepared by hydrosilylating {2-(X-phenyl)propyl}dichlorosilanes of formula I-2 (wherein X is H, C$_1$-C$_4$ alkyl, phenyl, fluoro, chloro or bromo group) with allylalkylsilanes of formula II-3 (Korean Patent Application number 93-26069 (Dec. 17, 1993)) in the presence of chloroplatinic acid catalyst. The products are the compounds of the formula III, wherein A is —(CH$_2$)$_2$—, R$^1$ is —(CH$_2$)$_3$R$^3$ (wherein R$^3$ is Ph, —CH$_2$Cl, —(CH$_2$)$_y$CH$_3$(y=0– 15), —CF$_3$, —CH$_2$CF$_3$, —SiMe$_m$Cl$_{3-m}$(m=0–3), —CN, —CH$_2$CN, —(p-Ph)CH$_2$Cl or 3-cyclohexenyl group) and R$^2$ is (X—Ph)CH(CH$_3$)CH$_2$— (wherein X is same as defined above).

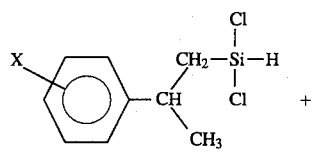

formula I-2

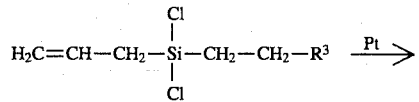

formula II-3

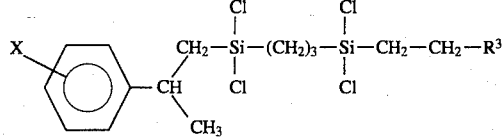

As an another embodiment of the present invention, α-[{2-(X-phenyl)propyl}dichlorosilyl]-ω-(dichloromethylsilyl)hexane or α-[{2-(X-phenyl)propyl} dichlorosilyl]-ω-(dichloromethylsilyl)octanes can be prepared by hydrosilylating {2-(X-phenyl)propyl}dichlorosilanes of formula I-2 (wherein X is hydrogen, C$_1$-C$_4$ alkyl, phenyl, fluoro, chloro or bromo group) with 1-(dichloromethylsilyl)- 5-hexene or 1-(dichloromethylsilyl)-7-octene of formula II-4 respectively in the presence of chloroplatinic acid catalyst. The bis(silyl)hexanes or bis(silyl)octanes are the bis(dichloroorganosilyl)alkanes of the formula III, wherein A is —(CH$_2$)$_n$—, R$^1$ is methyl and R$^2$ is —(X—Ph)CH(CH$_3$)CH$_2$— (wherein X is same as defined above).

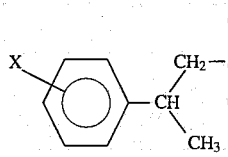

formula I-2

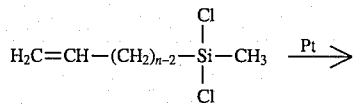

formula II-4

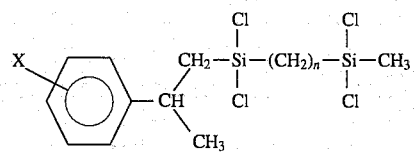

The 1-(dichloromethylsilyl)-5-hexene and 1-(dichloromethylsilyl)-7-octene can be prepared by hydrosilylating methyldichlorosilane with excess 1,5-hexadiene or 1,7-octadiene respectively in the presence of chloroplatinic acid catalyst.

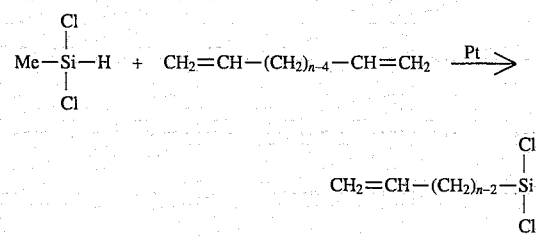

wherein n=6 or 8.

In the present invention, α,ω-bis[{2-(X-phenyl)propyl}dichlorosilyl]hexanes or α,ω-bis[{2-(X-phenyl)propyl}dichlorosilyl]diethylbenzenes can be prepared by hydrosilylating 1,5-hexadiene or divinylbenzene of formula II-5 with {2-(X-phenyl)propyl}dichlorosilanes (wherein X is hydrogen, $C_1$-$C_4$ alkyl, phenyl, fluoro, chloro or bromo group) of formula I-5 in the presence of chloroplatinic acid catalyst. The bis(silyl)hexanes or bis(silyl)octanes are the bis(dichloroorganosilyl)alkanes of the formula III, wherein A is —$(CH_2)_6$— or —$(CH_2)_2Ph(CH_2)_2$— and $R^1$ and $R^2$ are (X—Ph)CH(CH$_3$)CH$_2$— (wherein X is same as defined above), respectively.

$H_2C=CH-D-CH=CH_2$ + formula II-5

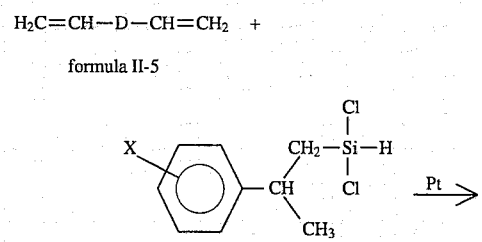

formula I-2

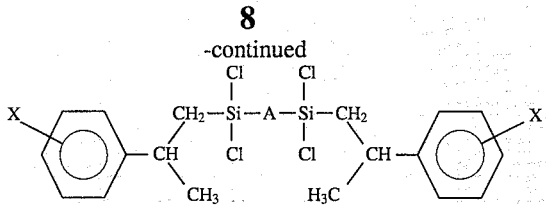

In the present invention, α-[{2-(X-phenyl)propyl}dichlorosilyl]-ω-(methyldichlorosilyl)diethylbenzenes can be prepared by hydrosilylating {2-(X-phenyl)propyl}dichlorosilanes of formula I-2 (wherein X is hydrogen, $C_1$-$C_4$ alkyl, phenyl, fluoro, chloro or bromo group) with α-(vinylphenyl)-ω-(dichloromethylsilyl)ethanes of formula II-6 in the presence of chloroplatinic acid catalyst. The bis(silyl)hexanes or bis(silyl)octanes are the bis(dichloroorganosilyl)alkanes of the formula III, wherein A is —$(CH_2)_2$—Ph—$(CH_2)_2$—, $R^1$ is methyl and $R^2$ is (X—Ph)CH(CH$_3$)CH$_2$— (wherein X is same as defined above).

The α,ω-(vinylphenyl)-ω-(dichloromethylsilyl)ethanes can be prepared by hydrosilylating methyldichlorosilane with excess divinylbenzene in the presence of chloroplatinic acid catalyst.

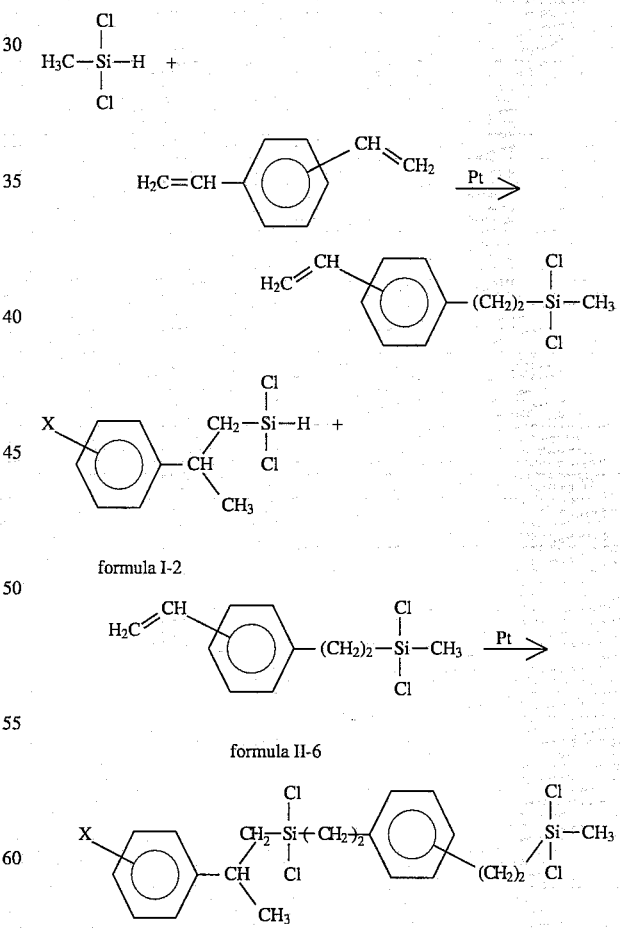

formula II-6

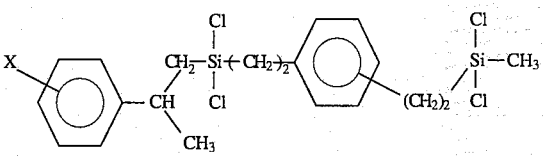

The invention will be further illustrated by the following examples. It is, however, not intended that this invention will be limited by the examples.

EXAMPLE 1

Synthesis of Bis {(3-Chloropropyl)Dichlorosilyl]Methane

To a 100 ml, three neck, round bottomed flask equipped with a dropping funnel and a reflux condenser, 6 g(0.03 mole) of bisdichlorosilylmethane, 6.5 g(0.08 mole) of allyl chloride, and 60 µl of 1% chloroplatinic acid solution in isopropanol, at reflux using a 80° C. oil bath for 3 hours under the dry nitrogen atmosphere. Gas chromatography analysis showed that no bisdichlorosilylmethane was left. Vacuum distillation of the reaction products gave 3.85 g(110°–112° C./0.05 mmHg) of bis{( 3-chloropropyl)dichlorosilyl]methane in 35.6% yield. Besides this product, 4.10 g of (trichlorosilyl){(3-chloropropyl)silyl}methane was also obtained in 38.0% yield and (propyldichlorosilyl){(3-chloropropyl)dichlorosilyl}methane.

EXAMPLE 2

Synthesis of Bis(Hexyldichlorosilyl)Methane

In the same apparatus and procedures as EXAMPLE 1, 8 g(0.04 mole) of bisdichlorosilylmethane, 12.7 g (0.15 mole) of 1-hexene and 120 µl of 1% chloroplatinic acid solution in isopropanol were placed and reacted for 2 hours at reflux under the dry nitrogen atmosphere. Vacuum distillation of the reaction products gave 11.1 g (118°–120° C./0.05 mmHg) of bis(hexyldichlorosilyl)methane in 72.6% yield.

EXAMPLE 3

Synthesis of [{3-(Trimethylsilyl)Propyl}Dichlorosilyl]Methane

In the same apparatus and procedures as EXAMPLE 1, 9.3 g (0.04 mole) of bisdichlorosilylmethane, 13.7 g (0.12 mole) of allyltrimethylsilane, and 80 µl of 1% chloroplatinic acid solution in isopropanol were placed and reacted for 2 hours at reflux under the dry nitrogen atmosphere. Vacuum distillation gave 13.3 g (134°–136 ° C./0.05 mmHg) of [{3-(trimethylsilyl)propyl}dichlorosilyl]methane in 75.1% yield.

The structures and $^1$H-NMR data of the compounds prepared using the same procedure as described above examples are listed in Table 1.

EXAMPLE 4

Synthesis of 1-(Methyldichlorosilyl)-2-{(2-Phenylpropyl)Dichlorosilyl]Ethane

In the same apparatus and procedures as EXAMPLE 1, 10 g (0.045 mole) of 3-(phenyl)-1, 1-dichloro-1-silabutane and 70 µl of 1% chloroplatinic acid solution in isopropanol were placed and 6.44 g (0.045 mole) of vinyldichloromethylsilane was added dropwise for 10 min. The solution was reacted for 2.5 hours at reflux under the dry nitrogen atmosphere. Vacuum distillation gave 11.7 g (100°–102° C./0.05 mmHg) of 1-(methyldichlorosilyl)-2-{(2-phenylpropyl)dichlorosilyl}ethane in 72.2% yield.

TABLE 1

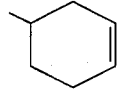

| R | CH$_2$(S) | CH$_2$ and R |
|---|---|---|
| CH$_2$Cl | 1.27 | 1.36–1.42(m, 4H, CH$_2$), 1.97–2.07(m, 4H, CH$_2$), 3.60(t, 4H, CH$_2$) |
| CN | 1.26 | 1.39–1.45(m, 4H, CH$_2$), 2.60(t, 4H, CH$_2$) |
| CH$_2$CN | 1.29 | 1.37–1.43(m, 4H, CH$_2$), 1.88–1.98(m, 4H, CH$_2$), 2.49(t, 4H, CH$_2$) |
| CH$_2$CF$_3$ | 1.25 | 1.30–1.38(m, 4H, CH$_2$), 1.86–1.96(m, 4H, CH$_2$), 2.33–2.69(m, 4H, CH$_2$) |
| CH$_3$ | 1.15 | 1.25–1.59(m, 8H, CH$_2$), 0.99(t, 3H, CH$_3$) |
| (CH$_2$)$_3$CH$_3$ | 0.92 | 0.82–0.93(m, 4H, CH$_2$), 1.18–1.25(m, 6H, CH$_2$). 1.30–1.45(m, 6H, CH$_2$) 1.51–1.61(m, 4H, CH$_2$), 1.33(t, 6H, CH$_3$) |
| cyclohexenyl | 1.12 | 1.50–1.55(m, 4H, CH$_2$), 1.21–1.57(m, 4H, CH$_2$), 1.48–1.79(m, 6H, CH, CH$_2$) 2.10–2.15(m, 8H, CH$_2$), 5.30–5.80(m, 4H, CH) |
| Ph | 1.50 | 1.68–1.73(m, 4H, CH$_2$), 2.85–2.92(m, 4H, CH$_2$), 7.21–7.33(m, 10H, phenyl-H) |
| CH$_2$SiMe$_3$ | 0.08 | 0.63–0.68(m, 4H, CH$_2$), 1.24–1.32(m, 4H, CH$_2$), 1.53–1.64(m, 4H, CH$_2$) 0.02(s, 18H, CH$_3$) |
| CH$_2$SiMeCl$_2$ | 0.12 | 0.65–0.73(m, 4H, CH$_2$), 1.33–1.38(m, 4H, CH$_2$), 1.58–1.66(m, 4H, CH$_2$) 0.83(s, 6H, CH$_3$) |

EXAMPLE 5

Synthesis of 1-(Methyldichlorosilyl)-2-[{(2-Methylphenyl)Propyl}-Dichlorosilyl]Ethane In the same apparatus and procedures as EXAMPLE 1, 8.5 g (0.037 mole) of 3-(methylphenyl)-1,1-dichloro-1-silabutane and 90 µl of 1% chloroplatinic acid solution in isopropanol were placed and then 5.16 g (0.037 mole) of vinyldichloromethylsilane was added dropwise for 10 min. The solution was reacted for 3 hours at reflux under the dry nitrogen atmosphere. Vacuum distillation gave 10.5 g (105°–107° C./mmHg) of 1-(methyldichlorosilyl)-2-[{(2-methylphenyl)propyl}-dichlorosilyl]ethane in 76.1% yield.

EXAMPLE 6

Synthesis of 1-(Methyldichlorosilyl)-2-[{2-(Fluorophenyl)Propyl}-Dichlorosilyl]Ethane In the same apparatus and procedures as EXAMPLE 1, 12.5 g (0.053 mole) of 3-(fluorophenyl)-1,1-dichloro-1-silabutane and 100 μl of 1% chloroplatinic acid solution in isopropanol were placed and then 7.43 g (0.053 mole) of vinyldichloromethylsilane was added dropwise for 10 min. The solution was reacted for 4 hours at reflux under the dry nitrogen atmosphere. Vacuum distillation gave 15.3 g (104°–106° C./mmHg) of 1-(methyldichlorosilyl)-2-[{2-(fluorophenyl)propyl}-dichlorosilyl]ethane in 76.5% yield.

The structures and $^1$H-NMR data of the compounds prepared using the same procedure as described above examples are listed in Table 2.

EXAMPLE 7

Synthesis of α-[{(3-Chloropropyl)Dichloro}Silyl]-ω-{(2-Phenylpropyl)-Dichlorosilyl]propane In the same apparatus and procedures as EXAMPLE 1, 5.3 g (0.024 mole) of 3-(phenyl)-1, 1-dichloro-1-silabutane and 100 μl of 1% chloroplatinic acid solution in isopropanol were placed and then 5.2 g (0.024 mole) of allyldichloro(3-chloropropyl)silane was added dropwise for 10 min. The solution was reacted for 2 hours at reflux under the dry nitrogen atmosphere. Vacuum distillation gave 5.46 g (158°–160° C./mmHg) of α-[{(3-chloropropyl)dichloro}silyl]-ω-{(2-phenylpropyl)-dichlorosilyl]propane in 52.1% yield.

EXAMPLE 8

Synthesis of α-[{2-(Dimethylchlorosilyl)Ethyl}Dichlorosilyl]-ω-[{2-(Methylphenyl)Propyl}Dichlorosilyl]Propane In the same apparatus and procedures as EXAMPLE 1, 4.7 g (0.020 mole) of 3-(methylphenyl)-1,1-dichloro-1-silabutane and 120 μl of 1% chloroplatinic acid solution in isopropanol were placed and then 10 g (0.020 mole) of allyldichloro{2-(chlorodiemthylsilyl)ethyl}silane was added dropwise for 10 min. The solution was reacted for 6 hours at room temperature under the dry nitrogen atmosphere. Vacuum distillation gave 6.5 g (150°–152° C./0.05 mmHg) of α-[{2-(dimethylchlorosilyl)ethyl}-dichlorosilyl]-ω-[{2-(methylphenyl)propyl}dichlorosilyl]propane in 67.6% yield.

EXAMPLE 9

Synthesis of α-[{2-(Dichloromethylsilyl)Ethyl}Dichlorosilyl]-ω-[{(2-Fluorophenyl)Propyl}Dichlorosily]Propane In the same apparatus and procedures as EXAMPLE 1, 7.6 g (0.029 mole) of 3-(fluorophenyl)-1,1-dichloro-1-silabutane and 80 μl of 1% chloroplatinic acid solution in isopropanol were placed and then 8.5 g (0.029 mole) of allyldichloro{2-(dichloromethylsilyl)ethyl}silane was added dropwise for 10 min. The solution was reacted for 4 hours at room temperature under the dry nitrogen atmosphere. Vacuum distillation gave 10.7 g (158°–160° C./0.05 mmHg) of α-[{2-(dichloromethylsilyl)ethyl}-dichlorosilyl]-ω-[{(2-fluorophenyl)propyl}dichlorosilyl]propane in 70.9% yield.

The structures and $^1$H-NMR data of the compounds prepared using the same procedure as described above examples are listed in Table 3.

TABLE 2

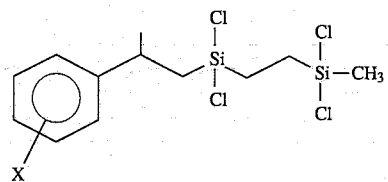

| Substituents X | CH$_3$(d) | CH(hex.) | CH$_2$ | aryl-H(m) | CH$_3$(s) | X |
|---|---|---|---|---|---|---|
| H | 1.40 | 3.12 | 0.90–1.00(m, 2H), 1.53–1.68(m, 2H), 2.36(d, 2H) | 7.05–7.26 | 0.70 | • |
| Me | 1.42 | 3.11 | 0.92–1.00(m, 2H), 1.55–1.69(m, 2H), 2.43(d, 2H) | 6.99–7.15 | 0.70 | 2.42(s, 3H, CH$_3$) |
| Et | 1.42 | 3.10 | 0.91–1.03(m, 2H), 1.54–1.66(m, 2H), 2.31(d, 2H) | 7.01–7.20 | 0.72 | 1.27(t, 3H, CH$_3$) 2.83(q, 2H, CH$_2$) |
| i-Pr | 1.41 | 3.05 | 0.80–0.89(m, 2H), 1.44–1.53(m, 2H), 2.20(d, 2H) | 6.80–7.01 | 0.58 | 1.29(d, 6H, CH$_3$) 2.93(hept., 1H, CH) |
| F | 1.44 | 3.13 | 0.99–1.10(m, 2H), 1.63–1.72(m, 2H), 2.53(d, 2H) | 7.00–7.25 | 0.82 | • |
| Cl | 1.40 | 3.07 | 0.95–1.03(m, 2H), 1.60–1.68(m, 2H), 2.48(d, 2H) | 6.93–7.18 | 0.78 | • |
| Br | 1.39 | 3.12 | 0.92–1.00(m, 2H), 1.55–1.63(m, 2H), 2.40(d, 2H) | 6.92–7.19 | 0.77 | • |

TABLE 3

Structure: aryl (with X substituent) - CH(CH₃) - CH₂ - CH₂ - Si(Cl)(Cl) - CH₂ - CH₂ - R (with additional SiCl₂ group per image)

| Substituents | | | | NMR data(ppm) | |
|---|---|---|---|---|---|
| X | R | CH₃(d) | CH(hex.) | aryl-H(m) | CH₂(m) and R | X |
| H | CH₂Cl | 1.40 | 3.15 | 7.21–7.36 | 0.63–0.80(m, 2H, CH₂), 1.00–1.07(m, 2H, CH₂), 1.93–2.03(m, 2H, CH₂), 3.59(t, 2H, CH₂), 1.48–1.65(m, 4H, CH₂), 1.20–1.25(m, 2H, CH₂) | • |
| H | CH₃ | 1.38 | 3.18 | 7.23–7.40 | 0.71–0.75(m, 2H, CH₂), 0.87(t, 3H, CH₃), 1.22–1.40(m, 4H, CH₂), 1.43–1.62(m, 2H, CH₂), 0.99–1.13(m, 4H, CH₂) | • |
| H | (CH₂)₃CH₃ | 1.38 | 3.17 | 7.21–7.39 | 0.64–0.81(m, 6H, CH₂), 0.98–1.09(m, 4H, CH₂), 1.22–1.31(m, 6H, CH₂), 1.47–1.65(m, 6H, CH₂), 0.92(t, 3H, CH₃) | • |
| H | CN | 1.43 | 3.19 | 7.07–7.36 | 0.81–0.93(m, 2H, CH₂), 2.48(t, 2H, CH₂), 1.00–1.13(m, 4H, CH₂), 1.31–1.42(m, 2H, CH₂), 1.55–1.68(m, 2H, CH₂) | • |
| H | (CH₂)₄CH=CH₂ | 1.39 | 3.19 | 7.12–7.32 | 0.70–0.82(m, 2H, CH₂), 0.95–1.05(m, 4H, CH₂), 1.20–1.37(m, 10H, CH₂), 1.45–1.64(m, 2H, CH₂), 1.88–2.17(m, 2H, CH₂), 4.80–5.10(m, 2H, CH₂), 5.47–6.08(m, 1H, CH) | • |
| H | Ph | 1.38 | 3.16 | 7.02–7.33 | 1.07–1.16 and 2.62–2.70(m, 2H, CH₂), 0.89–1.00(m, 4H, CH₂), 1.20–1.29(m, 2H, CH₂), 1.45–1.63(m, 2H, CH₂), 7.02–7.35(m, 5H, aryl-H) | • |
| H | 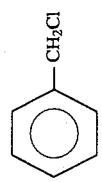 (CH₂Cl-phenyl) | 1.38 | 3.14 | 7.00–7.31 | 1.09–1.15 and 2.60–2.70(m, 2H, CH₂)7.01–7.31(m, 4H, aryl-H)4.53(s, 2H, CH₃), 1.46–1.60(m, 2H, CH₂), 0.99–1.15(m, 4H, CH₂), 1.28–1.35(m, 2H, CH₂) | • |
| H | CH₂CF₃ | 1.39 | 3.21 | 7.17–7.37 | 0.71–0.78(m, 2H, CH₂), 0.89–0.95(m, 4H, CH₂), 1.66–1.80(m, 2H, CH₂), 1.48–1.64(m, 2H, CH₂), 2.03–2.37(m, 2H, CH₂), 1.20–1.30(m, 2H, CH₂) | • |
| H |  (cyclohexenyl) | 1.41 | 3.20 | 7.17–7.31 | 0.74–0.82(m, 2H, CH₂), 0.99–1.10(m, 4H, CH₂), 1.22–1.31(m, 2H, CH₂), 1.46–1.59(m, 2H, CH₂), 1.48–2.23(m, 9H, CH₂ and CH)5.50–5.70(m, 2H, CH) | • |
| H | CH₂SiMe₃ | 1.38 | 3.18 | 7.07–7.35 | 0.01(s, 9H, CH₃), 0.61–0.65(m, 2H, CH₂), 1.07–1.15(m, 2H, CH₂), 1.50–1.61(m, 2H, CH₂), 0.95–1.05(m, 4H, CH₂), 1.46–1.60(m, 2H, CH₂), 1.21–1.31(m, 2H, CH₂) | • |
| Me | CH₂Cl | 1.39 | 3.13 | 7.05–7.25 | 0.71–0.93(m, 2H, CH₂), 1.69–1.81(m, 2H, CH₂), 3.38(t, 2H, CH₂), 0.99–1.10(m, 4H, CH₃), 1.55–1.60(m, 2H, CH₂), 1.30–1.41(m, 2H, CH₂) | 2.35(s, 3H, CH₃) |
| Me | SiMe₂Cl | 1.40 | 3.16 | 7.05–7.34 | 0.41(s, 6H, CH₃), 0.76–1.20(m, 4H, CH₃), 0.99–1.12(m, 4H, CH₂), 1.30–1.38(m, 2H, CH₂), 1.47–1.59(m, 2H, CH₂) | 2.37(s, 3H, CH₃) |
| Me | SiMeCl₂ | 1.40 | 3.15 | 7.07–7.28 | 0.79(s, 3H, CH₃), 1.08–1.22(m, 4H, CH₂), 0.95–1.05(m, 4H, CH₂), 1.25–1.31(m, 2H, CH₂), 1.55–1.62(m, 2H, CH₂) | 2.38(s, 3H, CH₃) |
| Me | SiCl₃ | 1.41 | 3.13 | 7.05–7.29 | 0.98–1.76(m, 10H, CH₂), 1.53–1.60(m, 2H, CH₂) | 2.36(s, 3H, CH₃) |

TABLE 3-continued

![structure: aryl (with X substituent) – CH(CH3) – CH2 – Si(Cl)(Cl) – CH2CH2CH2 – Si(Cl)(Cl) – CH2 – R]

| Substituents | | | | NMR data(ppm) | |
|---|---|---|---|---|---|
| X | R | CH₃(d) | CH(hex.) | aryl-H(m) | CH₂(m) and R | X |
| Me | (CH₂)₃CH₃ | 1.35 | 3.09 | 7.01–7.75 | 0.60–0.78(m, 2H, CH₂), 0.89(t, 3H, CH₃), 0.99–1.10(m 4H, CH₂) 1.15–1.61(m, 12H, CH₂) | 2.33(s, 3H, CH₃) |
| Et | CH₂SiCl₃ | 1.39 | 3.13 | 7.04–7.29 | 0.97–1.75(m, 12H, CH₂) | 1.25(t, 3H, CH₃) 2.81(q, 2H, CH₃) |
| Et | (CH₂)₄CH₃ | 1.35 | 3.09 | 7.02–7.23 | 0.60–0.74(m, 2H, CH₂), 0.88(t, 3H, CH₃), 0.98–1.10(m 4H, CH₂) 1.13–1.61(m, 12H, CH₂) | 1.24(t, 3H, CH₃) 2.82(q 2H, CH₃) |
| i-Pr | CH₂Cl | 1.39 | 3.15 | 6.95–7.30 | 0.72–0.79(m, 2H, CH₂), 0.99–1.10(m, 4H, CH₂), 1.33–1.40(m, 2H, CH₂) 1.56–1.60(m, 2H, CH₂), 1.70–1.76(m, 2H, CH₂), 3.35(t, 2H, CH₂) | 1.28(q, 6H, CH₃) 2.92(hep., 1H, CH) |
| i-Pr | SiMeCl₂ | 1.40 | 3.16 | 7.04–7.26 | 0.79(s, 3H, CH₃), 0.89–0.99(m, 4H, CH₂), 1.08–1.23(m, 4H, CH₂) 1.22–1.31(m, 2H, CH₂), 1.54–1.63(m, 2H, CH₂) | 1.27(d, 6H, CH₃) 2.91(hep., 1H, CH) |
| Ph | CH₂Cl | 1.44 | 3.22 | 7.25–7.59 | 0.79–0.91(m, 2H, CH₂), 1.00–1.10(m, 4H, CH₂), 1.25–1.36(m, 2H, CH₂) 1.59–1.64(m, 2H, CH₂), 1.76–1.94(m, 2H, CH₂), 3.25(t, 2H, CH₂) | 7.27–7.61 (m, 5H, phenyl-H) |
| F | SiMeCl₂ | 1.38 | 3.17 | 7.02–7.26 | 1.11–1.27(m, 2H, CH₂), 1.67–1.75(m, 2H, CH₂), 0.90–1.00(m, 4H, CH₂) 1.51–1.59(m, 2H, CH₂), 1.22–1.31(m, 2H, CH₂) | |
| Cl | CH₂Cl | 1.37 | 3.13 | 7.10–7.40 | 0.88–1.00(m, 6H, CH₂), 1.77–1.90(m, 2H, CH₂), 3.41(t, 2H, CH₂) 1.53–1.59(m, 2H, CH₂), 1.31–1.40(m, 2H, CH₂) | |
| Br | SiMe₂ | 1.39 | 3.20 | 7.02–7.44 | 0.62–0.68(m, 2H, CH₂), 0.98–1.16(m, 6H, CH₂), 1.23–1.33(m, 2H, CH₂) 1.47–1.60(m, 2H, CH₂) | |

EXAMPLE 10

Synthesis of α-(Methyldichlorosilyl)-ω-{(2-Phenylpropyl)-Dichlorosilyl}Hexane

In the same apparatus and procedures as EXAMPLE 1, 10 g (0.046 mole) of 3-(phenyl)-1,1-dichloro-1-silabutane and 100 μl of 1% chloroplatinic acid solution in isopropanol were placed and then 9.1 g (0.046 mole) of 1-(methyldichlorosilyl)-5-hexene was added dropwise for 10 min. The solution was reacted for 5 hours at reflux under the dry nitrogen atmosphere. Vacuum distillation gave 14.9 g (160°–162 ° C./0.05 mmHg) of α-(methyldichlorosilyl)-ω-{(2-phenylpropyl)dichlorosilyl}hexane in 77.8% yield.

EXAMPLE 11

Synthesis of α-(Methyldichlorosilyl)-ω-[{2-(Methylphenyl)propyl}-Dichlorosilyl]Hexane In the same apparatus and procedures as EXAMPLE 1, 19.9 g (0.086 mole) of 3-(methylphenyl)-1,1-dichloro-1-silabutane and 90 μl of 1% chloroplatinic acid solution in isopropanol were placed and then 17 g (0.086 mole) of 1-(methyldichlorosilyl)- 5-hexene was added dropwise for 10 min. The solution was reacted for 2.5 hours at reflux under the dry nitrogen atmosphere. Vacuum distillation gave 27.8 g(165°–167° C./0.05 mmHg) of α-(methyldichlorosilyl)-ω-[{2 -(methylphenyl)propyl}dichlorosilyl]hexane in 75.1% yield.

EXAMPLE 12

Synthesis of α-(Methyldichlorosilyl)-ω-[{2-(Ethylphenyl)Propyl}-Dichlorosilyl]Hexane In the same apparatus and procedures as EXAMPLE 1, 20.0 g (0.081mole) of 3-(ethylphenyl)-1,1-dichloro-1-silabutane and 80 μl of 1% chloroplatinic acid solution in isopropanol were placed and then 16 g (0.081 mole) of 1-(methyldichlorosilyl)- 5-hexene was added dropwise for 10 min. The solution was reacted for 2 hours at room temperature under the dry nitrogen atmosphere. Vacuum distillation gave 25.1 g (170°–172° C./0.05 mmHg) of α-(methyldichlorosilyl)-ω-[{2 -(ethylphenyl)propyl}dichlorosilyl]hexane in 69.7% yield.

The structures and ¹H-NMR data of the compounds prepared using the same procedure as described above examples are listed in Table 4.

EXAMPLE 13

Synthesis of α-(Methyldichlorosilyl)-ω-{(2-Phenylpropyl)-Dichlorosilyl]octane

In the same apparatus and procedures as EXAMPLE 1, 5.0 g (0.02 mole) of 3-(phenyl)-1,1-dichloro-1-silabutane and 60 μl of 1% chloroplatinic acid solution in isopropanol were placed and then 4.5 g (0.02 mole) of 1-(dichloromethylsilyl)-7-octene was added dropwise for 10 min. The solution was reacted for 4 hours at reflux under the dry nitrogen atmosphere. Vacuum distillation gave 6.8 g (164°–166° C./0.03 mmHg) of α-(methyldichlorosilyl)-ω-{(2-phenylpropyl)dichlorosilyl}octane in 76.6% yield.

EXAMPLE 14

Synthesis of a-(Methyldichlorosilyl)-w-[{2-(Methylphenyl)Propyl}-Dichlorosilyl]Octane In the same apparatus and procedures as EXAMPLE 1, 10 g (0.043 mole) of 3-(methylphenyl)-1,1-dichloro-1-silabutane and 80 μl of 1% chloroplatinic acid solution in isopropanol were placed and then 9.7 g (0.043 mole) of 1-(dichloromethylsilyl)- 7-octene was added dropwise for 10 min. The solution was reacted for 4 hours at reflux under the dry nitrogen atmosphere. Vacuum distillation gave 19.7 g (168°–170° C./0.03 mmHg) of α-(methyldichlorosilyl)-ω-[{2-(methylphenyl)propyl}dichlorosilyl]octane in 76.1% yield.

TABLE 4

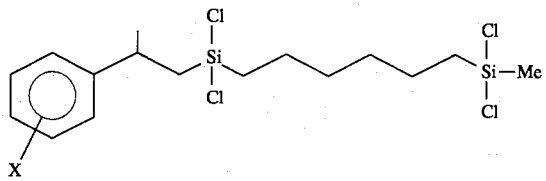

| Substituents X | CH₃(d) | CH(hex.) | CH₂(m) | aryl-H(m) | CH₃(s) | X |
|---|---|---|---|---|---|---|
| H | 1.39 | 3.15 | 0.57–0.76(2H), 1.07–1.16(2H), 1.16–1.34(6H) 1.41–1.58(4H) | 7.11–7.35 | 0.79 | |
| Me | 1.42 | 3.17 | 0.67–0.80(2H), 1.10–1.16(2H), 1.27–1.39(6H) 1.46–1.65(4H) | 7.06–7.27 | 0.82 | 2.39(s, 3H, CH₃) |
| Et | 1.40 | 3.16 | 0.68–0.82(2H), 1.10–1.18(2H), 1.28–1.40(6H) 1.48–1.66(4H) | 7.03–7.33 | 0.79 | 1.26(t, 3H, CH₃) 2.64(q, 2H, CH₂) |
| i-Pr | 1.41 | 3.16 | 0.59–0.70(2H), 1.11–1.18(2H), 1.33–1.48(6H) 1.46–1.66(4H) | 7.04–7.28 | 0.78 | 1.27(d, 6H, CH₃) 2.91(hept., 1H, CH) |
| Ph | 1.47 | 3.24 | 0.79–0.91(2H), 1.20–1.31(2H), 1.34–1.52(6H) 1.59–1.64(4H) | 7.27–7.61 | 0.85 | 7.27–7.61(m, 5H, phenyl-H) |
| F | 1.44 | 3.18 | 0.68–0.85(2H), 1.18–1.24(2H), 1.20–1.38(6H) 1.54–1.69(4H) | 7.00–7.61 | 0.92 | • |
| Cl | 1.39 | 3.15 | 0.67–0.81(2H), 1.11–1.23(2H), 1.30–1.39(6H) 1.52–1.68(4H) | 7.13–7.42 | 0.79 | • |
| Br | 1.38 | 3.20 | 0.69–0.80(2H), 1.08–1.35(2H), 1.27–1.48(6H) 1.47–1.60(4H) | 7.02–7.44 | 0.77 | • |

EXAMPLE 15

Synthesis of α-(Methyldichlorosilyl)-ω[{2-(Ethylphenyl)-Propyl}Dichlorosilyl]Octane In the same apparatus and procedures as EXAMPLE 1, 20 g (0.081 mole) of 3-(ethylphenyl)-1,1-Dichlorol-silabutane and 140 μl of 1% chloroplatinic acid solution in isopropanol were placed and then 18.2 g (0.081 mole) of 1-(dichloromethylsilyl)- 7-octene was added dropwise for 10 min. The solution was reacted for 2.5 hours at reflux under the dry nitrogen atmosphere. Vacuum distillation gave 28.7 g (175°–177° C./0.03 mmHg) of α-(methyldichlorosilyl)-ω-[{2 -(ethylphenyl)propyl}dichlorosilyl]octane in 75.0% yield.

The structures and ¹H-NMR data of the compounds prepared using the same procedure as described above examples are listed in Table 5.

EXAMPLE 16

Synthesis of Bis{(2-Phenylpropyl)Dichlorosilyl}Hexane

In the same apparatus and procedures as EXAMPLE 1, 21.3 g (0.097 mole) of 3-(phenyl)-1,1-dichloro-1-silabutane and 100 μl of 1% chloroplatinic acid solution in isopropanol were placed and then 3.2 g (0.039 mole) of 1,5-hexadiene was added dropwise for 5 min. The solution was reacted for 15 hours at reflux under the dry nitrogen atmosphere. Vacuum distillation gave 13.4 g (185°–187° C./0.03 mmHg) of bis{(2-phenylpropyl)dichlorosilyl}hexane in 66.0% yield.

EXAMPLE 17

Synthesis of Bis[{2-(Methylphenyl)Propyl}Dichlorosilyl]Hexane

In the same apparatus and procedures as EXAMPLE 1, 20.8 g (0.089 mole) 3-(methylphenyl)-1,1-dichloro-1-silabutane and 90 μl of 1% chloroplatinic acid solution in isopropanol were placed and then 3.0 g (0.036 mole) of 1,5-hexadiene was added dropwise for 3 min. The solution was reacted for 13 hours at reflux under the dry nitrogen atmosphere. Vacuum distillation gave 15.2 g (189°–191° C./0.03 mmHg) of bis[{2-(methylphenyl)propyl}dichlorosilyl]hexane in 77.2% yield.

EXAMPLE 18

Synthesis of Bis[{2-(Ethylphenyl)Propyl}Dichlorosilyl]Hexane

In the same apparatus and procedures as EXAMPLE 1, 37.5 g (0.153 mole) of 3-(ethylphenyl)-1,1-dichloro-1-silabutane and 100 μl of 1% chloroplatinic acid solution in isopropanol were placed and then 5 g (0.061 mole) of 1,5-hexadiene was added dropwise for 5 min. The solution was reacted for 14 hours at reflux under the dry nitrogen atmosphere. Vacuum distillation gave 24.6 g (190°–192° C./0.03 mmHg) of bis[{2-(ethylphenyl)propyl}dichlorosilyl]hexane in 69.8% yield.

EXAMPLE 19

Synthesis of α,ω-Bis{(2-Phenylpropyl)Dichlorosilyl}Diethylbenzene

In the same apparatus and procedures as EXAMPLE 1, 18.5 g (0.084 mole) of 3-(phenyl)-1,1-dichloro-1-silabutane and 90 μl of 1% chloroplatinic acid solution in isopropanol were placed and then 5.0 g (0.038 mole) of divinylbenzene was added dropwise for 10 min. The solution was reacted for 6 hours at room temperature under the dry nitrogen atmosphere. Vacuum distillation gave 15.2 g (186°–188° C./0.03 mmHg) of bis{(2-phenylpropyl)dichlorosilyl}diethylbenzene in 70.4% yield.

The structures and ¹H-NMR data of the compounds prepared using the same procedure as described above examples are listed in Table 6.

TABLE 5

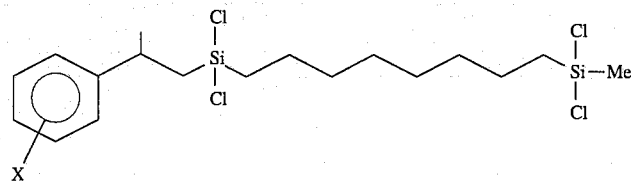

| Substituents X | CH₃(d) | CH(hex.) | CH₂(m) | aryl-H(m) | CH₃(s) | X |
|---|---|---|---|---|---|---|
| H | 1.39 | 3.15 | 0.61–0.76(2H), 1.10–1.16(4H), 1.23–1.34(6H) 1.47–1.83(4H) | 7.16–7.35 | 0.79 | • |
| Me | 1.42 | 3.16 | 0.66–0.78(2H), 1.08–1.23(4H), 1.22–1.30(6H) 1.56–1.63(4H) | 7.09–7.30 | 0.80 | 2.39(s, 3H, CH₃) |
| Et | 1.40 | 3.14 | 0.56–0.60(2H), 1.22–1.33(6H), 1.55–1.63(4H) 1.08–1.23(4H) | 7.08–7.29 | 0.80 | 1.26(s, 3H, CH₃) 2.81(q, 2H, CH₂) |
| i-Pr | 1.41 | 3.16 | 0.62–0.75(2H), 1.08–1.23(4H), 1.35–1.42(6H) 1.54–1.63(4H) | 7.04–7.28 | 0.79 | 1.27(d, 6H, CH₃) 2.91(hept., 1H, CH) |
| Ph | 1.44 | 3.21 | 0.61–0.76(2H), 1.10–1.20(4H), 1.33–1.42(6H) 1.59–1.64(4H) | 7.27–7.61 | 0.80 | 7.27–7.61(m, 5H, phenyl-H) |
| F | 1.40 | 3.19 | 0.69–0.80(2H), 1.12–1.27(4H), 1.67–1.75(6H) 1.51–1.59(4H) | 7.04–7.28 | 0.80 | • |
| Cl | 1.42 | 3.13 | 0.65–0.80(2H), 1.10–1.18(4H), 1.23–1.34(6H) 1.55–1.84(4H) | 7.12–7.37 | 0.82 | • |
| Br | 1.39 | 3.22 | 0.62–0.71(2H), 1.18–1.23(4H), 1.33–1.37(6H) 1.47–1.60(4H) | 7.02–7.44 | 0.79 | • |

EXAMPLE 20

Synthesis of α-(Methyldichlorosilyl)-ω-{(2-Phenylpropyl)-Dichlorosilyl}Diethylbenzene In the same apparatus and procedures as EXAMPLE 1, 10.7 g (0.049 mole) of 3-(phenyl)-1,1-dichloro-1-silabutane and 90 μl of 1% chloroplatinic acid solution in isopropanol were placed and then 12.0 g (0.049 mole) of α-(vinylphenyl)-ω-(dichloromethylsilyl)ethane was added dropwise for 10 min. The solution was reacted for 16 hours at 60° C. under the dry nitrogen atmosphere. Vacuum distillation gave 11.7 g (172°–174° C./0.03 mmHg) of α-(methyldichlorosilyl)-ω-{( 2-phenylpropyl)dichlorosilyl}diethylbenzene in 51.4% yield.

EXAMPLE 21

Synthesis of α-(Methyldichlorosilyl)ω-[{2-(Methylphenyl)Propyl}-Dichlorosilyl]Diethylbenzene In the same apparatus and procedures as EXAMPLE 1, 14.2 g (0.06 mole) of 3-(methylphenyl)-1,1-dichloro-1-silabutane and 80 μl of 1% chloroplatinic acid solution in isopropanol were placed and then 15 g(0.06 mole) of α-(vinylphenyl)-ω-(dichloromethylsilyl)ethane was added dropwise for 10 min. The solution was reacted for 15 hours at 60° C. under the dry nitrogen atmosphere. Vacuum distillation gave 14.3 g (176°–178° C./0.03 mmHg) of α-(methyldichlorosilyl)-ω-[{2-(methylphenyl)propyl}dichlorosilyl]diethylbenzene in 49.8% yield.

EXAMPLE 22

Synthesis of α-(Methyldichlorosilyl)-ω-[{2-(Ethylphenyl)Propyl}-Dichlorosilyl]Diethylbenzene In the same apparatus and procedures as XAMPLE 1, 10.1 g (0.041 mole) of 3-(ethylphenyl)-1,1-dichloro-1-silabutane and 80 μl of 1% chloroplatinic acid solution in isopropanol were placed and then 10 g (0.041 mole) of α-(vinylphenyl)-ω-(dichloromethylsilyl)ethane was added dropwise for 10 min. The solution was reacted for 13 hours at 60° C. under the dry nitrogen atmosphere. Vacuum distillation gave 10.7 g (182°–184° C./0.03 mmHg) of α-(methyldichlorosilyl)-ω-[{2-(ethylphenyl)propyl}dichlorosilyl]diethylbenzene in 53.0% yield.

The structures and $^1$H-NMR data of the compounds prepared using the same procedure as described above examples are listed in Table 7.

TABLE 6

| Substituents | | NMR data(ppm) | | | | |
|---|---|---|---|---|---|---|
| C | X | $CH_3$(d) | CH(hex.) | aryl-H(m) | $CH_3$(m) | X |
| —($CH_2$)2— | H | 1.41 | 3.16 | 7.21–7.39 | 0.63–0.71(2H), 1.09–1.18(2H), 1.21–1.31(2H), 1.54–1.59(2H) | • |
| " | Me | 1.43 | 3.13 | 7.12–7.33 | 0.62–0.71(2H), 1.10–1.19(2H), 1.23–1.33(2H), 1.60–1.71(2H) | 2.39(s, 3H, $CH_3$) |
| " | Et | 1.43 | 3.12 | 7.11–7.38 | 0.65–0.75(2H), 1.08–1.15(2H), 1.21–1.33(2H), 1.56–1.64(2H) | 1.26(t, 3H, $CH_3$) 2.82(q, 2H, $CH_2$) |
| " | i-Pr | 1.38 | 3.13 | 7.06–7.30 | 0.61–0.71(2H), 1.08–1.20(2H), 1.28–1.35(2H), 1.60–1.68(2H) | 1.27(d, 6H, $CH_3$) 2.91(hept., 1H, CH) |
| " | F | 1.45 | 3.15 | 7.08–7.30 | 0.70–0.79(2H) 1.13–1.75(6H) | • |
| " | Cl | 1.41 | 3.15 | 7.11–7.37 | 0.73–0.80(2H) 1.08–1.65(6H) | • |
| " | Br | 1.40 | 3.17 | 7.05–7.48 | 0.71–0.79(2H) 1.03–1.66(6H) | • |
| phenyl | H | 1.38 | 3.16 | 7.24–7.44 | 1.23–1.60(8H) 2.53–2.88(4H) | • |

TABLE 7

| Substituents X | $CH_3$(d) | CH(hex.) | $CH_2$(m) | aryl-H(m) | $CH_3$(s) | X |
|---|---|---|---|---|---|---|
| H | 1.38 | 3.17 | 1.02–1.07(2H), 1.21–1.57(6H), 2.52–2.83(2H) | 7.02–7.42 | 0.63 | • |
| $CH_3$ | 1.39 | 3.15 | 1.00–1.05(2H), 1.28–1.57(6H), 2.55–2.90(2H) | 6.96–7.40 | 0.60 | 2.38(s, 3H, $CH_3$) |

TABLE 7-continued

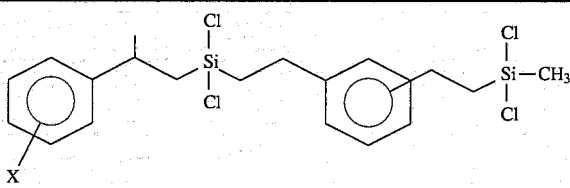

| Substituents X | CH₃(d) | CH(hex.) | CH₂(m) | aryl-H(m) | CH₃(s) | X |
|---|---|---|---|---|---|---|
| Et | 1.40 | 3.14 | 1.10–1.15(2H), 1.23–1.57(6H), 2.53–2.85(2H) | 6.83–7.28 | 0.64 | 1.27(t, 3H, CH₃) 2.92(q, 2H, CH₂) |
| i-Pr | 1.40 | 3.14 | 1.01–1.09(2H), 1.15–1.60(6H), 2.55–2.88(2H) | 6.79–7.20 | 0.79 | 1.27(d, 6H, CH₃) 2.91(hept., 1H, CH) |
| Ph | 1.44 | 3.24 | 1.09–1.15(2H), 1.31–1.68(6H), 2.59–2.98(2H) | 7.12–7.58 | 0.83 | 7.12–7.58(m, 5H, phenyl-H) |
| F | 1.38 | 3.18 | 1.02–1.08(2H), 1.21–1.58(6H), 2.53–2.85(2H) | 6.80–7.22 | 0.72 | • |
| Cl | 1.37 | 3.17 | 1.10–1.20(2H), 1.33–1.60(6H), 2.70–2.90(2H) | 7.00–7.42 | 0.69 | • |
| Br | 1.36 | 3.15 | 1.03–1.09(2H), 1.22–1.60(6H), 2.53–2.88(2H) | 6.82–7.24 | 0.65 | • |

What is claimed is:

1. The bis(dichloroorganosilyl)alkanes of formula III;

wherein $R^1$ and $R^2$ are same or different and is selected from the group consisting of —(CH₂)₂R³ (wherein $R^3$ represents Ph, —CH₂Cl, —(CH₂)ᵧCH₃(y=0–15), —CF₃, —CH₂CF₃, SiMe$_m$Cl$_{3-m}$(m=0–3), —CN, —CH₂CN, —(p-Ph)CH₂Cl or 3-cyclohexenyl group) or (X—Ph)CH(CH₃)CH₂— (wherein X represents hydrogen, C₁-C₄ alkyl, phenyl, fluoro, chloro or bromo group); or $R^1$ is —CH₃ or —(CH₂)₂R³ (wherein $R^3$ is same as defined above) and $R^2$ is (X—Ph)CH(CH₃)CH₂— (wherein X is same as defined above); and A is selected from the group consisting of —(CH₂)$_n$— (n=1, 2, 3, 6 or 8), or —(CH₂)₂Ph(CH₂)₂—.

2. The compounds in accordance with claim 1, wherein $R^3$ is Ph, —CH₂Cl, —(CH₂)ᵧCH₃ (y=0–15), —CF₃, —CH₂CF₃, —SiMe$_m$Cl$_{3-m}$(m=0–3), —CN, —CH₂CN, —(p-Ph)CH₂Cl or 3-cyclohexenyl group.

3. The compounds in accordance with claim 1, wherein $R^1$ is —CH₃ or —(CH₂)₂R³ (wherein $R^3$ represents alkyl with or without functional groups, aryl, silyl or cyano group) and $R^2$ is (X—Ph)CH(CH₃)CH₂— (wherin X represents hydrogen, C₁-C₄ alkyl, phenyl, fluoro, chloro or bromo group).

4. The compounds in accordance with claim 1, wherein A represents —(CH₂)$_n$—(n=1, 2, 3, 6 or 8) or —(CH₂)₂Ph(CH₂)₂—.

5. The compounds in accordance with claim 3, wherein $R^3$ is Ph, CH₂Cl, —(CH₂)ᵧCH₃ (y=0–15), —CF₃, —CH₂CF₃, —SiMe$_m$Cl$_{3-m}$(m=0–3), —CN, —CH₂CN, —(p-Ph)CH₂Cl or 3-cyclohexenyl group.

6. A process for the preparation of bis(dichloroorganosilyl)alkanes of formula III comprising hydrosilylating bis-(dichlorosilyl)methanes of formula I, with organoolefins or organosilylolefins of formula II in the presence of chloroplatinic acid catalyst;

wherein Q represents —SiHCl₂ or

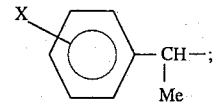

X represents hydrogen, C₁-C₄ alkyl, phenyl, fluoro, chloro or bromo group; and P represents $R^3$, —CH₂SiCl₂(CH₂)₂R³, —B—SiCl₂CH₃, or D—CH═CH₂ wherein $R^3$ represents Ph, —CH₂Cl, —(CH₂)ᵧCH₃(y=0–15), —CF₃, —CH₂CF₃, —SiMe$_m$Cl$_{3-m}$(m=0–3), —CN, —CN₂CN, —(p-Ph)CH₂Cl or 3-cyclohexenyl group, B is —(CH₂)$_n$— (wherein n=4 or 6) or —Ph(CH₂)₂— and D is —(CH₂)₂— or —Ph—.

7. The method in accordance with claim 6, wherein Q is SiHCl₂ and P is $R^3$ wherein $R^3$ is alkyl with or without functional groups, aryl, silyl or cyano group.

8. The method in accordance with claim 6, wherein Q is

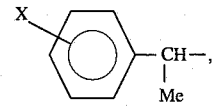

X is hydrogen, C₁-C₄ alkyl, phenyl, fluoro, chloro or bromo group and P is alkyl with or without functional groups, aryl, silyl or cyano group.

9. The method in accordance with claim 6, wherein Q is

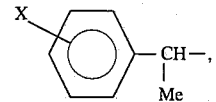

X is hydrogen, C₁-C₄ alkyl, phenyl, fluoro, chloro or bromo group, and P is —CH₂SiCl₂(C₂)₂R³ wherein $R^3$ is alkyl with or without functional groups, aryl, silyl or cyano group.

10. The method in accordance with claim 6, wherein Q is

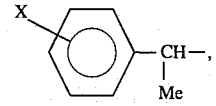

X is hydrogen, $C_1$-$C_4$ alkyl, phenyl, fluoro, chloro or bromo group, and P is —B—$SiCl_2CH_3$ wherein B is alkyl or aryl group.

11. The method in accordance with claim 6, wherein P is D—CH=$CH_2$ wherein D is alkyl or aryl group.

12. The method in accordance with claim 6, wherein the molar ratio of formula abd formula II is 2:1.

* * * * *